United States Patent [19]

Oku et al.

[11] Patent Number: 4,963,576
[45] Date of Patent: Oct. 16, 1990

[54] DITHIOACETAL COMPOUNDS, PROCESSES FOR PREPARATION THEREOF AND PHARMACEUTICAL COMPOSITION COMPRISING THE SAME

[75] Inventors: Teruo Oku; Yoshio Kawai; Hiroshi Kayakiri; Kazuyoshi Kuratani; Masashi Hashimoto, all of Tsukuba, Japan

[73] Assignee: Fujisawa Pharmaceutical Company, Ltd., Osaka, Japan

[21] Appl. No.: 191,253

[22] Filed: May 6, 1988

[30] Foreign Application Priority Data

May 19, 1987 [GB] United Kingdom ............... 8711802

[51] Int. Cl.⁵ ................ A61K 31/415; A61K 31/420; A61K 31/425; C07D 277/62
[52] U.S. Cl. .................................... 514/367; 514/375; 514/394; 514/395; 548/169; 548/178; 548/179; 548/217; 548/221; 548/329; 548/330; 548/327; 544/283; 546/121; 546/152; 546/339; 568/584; 568/659
[58] Field of Search ............... 548/168, 178, 179, 165, 548/169, 217, 221, 329, 330, 327; 514/367, 445, 375, 376, 387, 394, 395

[56] References Cited

U.S. PATENT DOCUMENTS 4,600,721 7/1986 Mörsdorf et al. .................. 514/367
4,730,005 3/1988 Gleason et al. .................... 514/445
4,732,986 3/1988 Brune et al. ....................... 548/161
4,794,188 12/1988 Musser et al. ...................... 546/152

FOREIGN PATENT DOCUMENTS 0181568 5/1986 European Pat. Off. .

Primary Examiner—Mukund J. Shaw
Assistant Examiner—Philip I. Datlow
Attorney, Agent, or Firm—Oblon, Spivak, McClelland, Maier & Neustadt

[57] ABSTRACT

The invention relates to dithioacetal compounds having 5-lipoxygenase-inhibiting activity, of the formula:

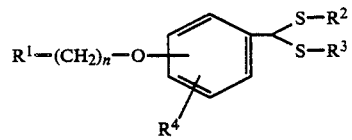

wherein
  $R^1$ is lower alkyl, di-(lower)alkylamino, aryl, or heterocyclic group which may have one or more substituents selected from halogen, lower alkyl, lower alkoxy and phenyl,
  $R^2$ and $R^3$ are each lower alkyl, aryl or ar-(lower)alkyl, or $R^2$ and $R^3$ are together to form 1,3-dithian ring,
  $R^4$ is hydrogen or lower alkoxy, and
  n is 0 or an integer 1 to 4 and pharmaceutically acceptable salts thereof.

11 Claims, No Drawings

DITHIOACETAL COMPOUNDS, PROCESSES FOR PREPARATION THEREOF AND PHARMACEUTICAL COMPOSITION COMPRISING THE SAME

This invention relates to new dithioacetal compounds and pharmaceutically acceptable salts thereof. More particularly, it relates to new dithioacetal compounds and pharmaceutically acceptable salts thereof which have 5-lipoxygenase-inhibiting activity, to processes for the preparation thereof and to a pharmaceutical composition comprising the same.

The objective dithioacetal compounds and pharmaceutically acceptable salts thereof are novel and can be represented by the following general formula (I):

$$R^1-(CH_2)_n-O-\text{Ar}(R^4)-CH(S-R^2)(S-R^3) \quad (I)$$

wherein
- $R^1$ is lower alkyl, di-(lower)alkylamino, aryl, or heterocyclic group which may have one or more substituents selected from halogen, lower alkyl, lower alkoxy and phenyl,
- $R^2$ and $R^3$ are each lower alkyl, aryl or ar(lower)alkyl, or $R^2$ and $R^3$ are together to form 1,3-dithian ring,
- $R^4$ is hydrogen or lower alkoxy, and n is 0 or an integer 1 to 4, and pharmaceutically acceptable salts thereof.

According to this invention, the new dithioacetal compounds (I) can be prepared by various processes which are illustrated by the following schemes:

Process 1

$$R^1-(CH_2)_n-Y + HO-\text{Ar}(R^4)-CH(S-R^2)(S-R^3) \longrightarrow$$
$$(II) \qquad (III)$$

$$R^1-(CH_2)_n-O-\text{Ar}(R^4)-CH(S-R^2)(S-R^3)$$
$$(I)$$

Process 2

$$R^1-(CH_2)_n-O-\text{Ar}(R^4)-CHO + R^2-SH \longrightarrow$$
$$(IV) \qquad (V)$$

$$R^1-(CH_2)_n-O-\text{Ar}(R^4)-CH(S-R^2)(S-R^2)$$
$$(I^a)$$

Process 3

$$R^1-(CH_2)_n-O-\text{Ar}(R^4)-CHO +$$
$$(IV)$$

$$SH-(CH_2)_3-SH \longrightarrow$$
$$(VI)$$

$$R^1-(CH_2)_n-O-\text{Ar}(R^4)-CH\underset{S}{\overset{S}{\diagdown}}(CH_2)_3$$
$$(I^b)$$

Process 4 benzimidazole(NH)-$(CH_2)_n$-O-Ar($R^4$)-CH(S-$R^2$)(S-$R^3$) $\longrightarrow$
$$(I^c)$$

benzimidazole(N-$R^5$)-$(CH_2)_n$-O-Ar($R^4$)-CH(S-$R^2$)(S-$R^3$)
$$(I^d)$$

In the above formulae, Y is an acid residue, $R^5$ is lower alkyl, and $R^1$, $R^2$, $R^3$, $R^4$ and n are as defined before.

Preferred pharmaceutically acceptable salts of the object compound (I) are conventional non-toxic salts and may include a salt with an acid such as a salt with an inorganic acid (e.g., hydrochloride, hydrobromide, sulfate, phosphate, etc.), or a salt with an organic carboxylic or sulfonic acid (e.g., formate, acetate, trifluoroacetate, maleate, tartrate, methanesulfonate, benzenesulfonate, p-toluenesulfonate, etc.).

Preferred examples and illustrations of the various definitions, in the above descriptions, which the present invention includes within the scope thereof are explained in detail as follows.

The term "lower" is intended to mean 1 to 6 carbon atoms, unless otherwise indicated.

Preferred examples of "lower alkyl" and lower alkyl moiety may include a residue of straight and branched alkane having 1 to 6 carbon atom(s) such as methyl, ethyl, propyl, isopropyl, butyl, isobutyl, t-butyl, pentyl, isopentyl, neopentyl, hexyl, isohexyl and the like.

Preferred examples of "lower alkoxy" may include methoxy, ethoxy, propoxy, isopropoxy, butoxy and the like.

Preferred examples of "aryl" and aryl moiety may include phenyl, tolyl, xylyl, naphtyl and the like.

Preferred examples of "heterocyclic group" may include a unsaturated 3- to 8-membered monocyclic heterocyclic group containing 1 to 4 nitrogen atoms such as pyrrolyl, pyrrolinyl, imidazolyl, pyrazolyl, pyridyl and its N-oxide, dihydropyridyl, pyrimidyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), and the like, a 3- to 8-membered monocyclic heterocyclic group containing at least one sulfur atom and at least one nitrogen atom such as thiazolyl, isothiazolyl, thiadiazolyl and the like, a polycyclic (e.g. bicyclic) heterocyclic group containing at least one nitrogen atom such as indolyl, isoindolyl, indolizinyl, benzimidazolyl, quinolyl, isoquinolyl, quinazolinyl, imidazo[1,2-a]-pyridyl and the like, a polycyclic (e.g. bicyclic) heterocyclic group containing at least one sulfur atom and at least one nitrogen atom such as benzothiazolyl, benzothiadiazolyl and the like, a polycyclic (e.g. bicyclic)heterocyclic group containing at least one oxygen atom such as benzofuranyl, isobenzofuranyl and the like, a polycyclic (e.g. bicyclic) heterocyclic group containing at least one oxygen atom and at least one nitrogen atom such as benzoxazolyl, benzoxadiazolyl and the like.

More preferred examples of "heterocyclic group" may include unsaturated benzene-fused 5 or 6-membered heterocyclic group containing one or two nitrogen atoms such as benzimidazolyl, quinolyl, isoquinolyl, quinazolinyl and the like, and unsaturated benzenefused 5 or 6-membered heterocyclic group containing one nitrogen atom and one sulfur or oxygen atom such as benzothiazolyl, benzoxazolyl and the like.

More preferred examples of "heterocyclic group" may be represented by the following formula:

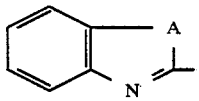

wherein A is

—O— or —S—.

Preferred examples of "halogen" is fluorine, chlorine, bromine and iodine.

Preferred examples of "acid residue" may include an acid residue of an inorganic acid (e.g. hydrochloric acid, hydrobromic acid, hydroiodic acid, sulfuric acid, etc.) an organic acid such as organic sulfonic acid (e.g. methanesulfonic acid, benzenesulfonic acid, toluenesulfonic acid, etc.), an organic carbamic acid (e.g. dimethylcarbamic acid, etc.) and the like.

Processes for preparing the object compound (I) of this invention are explained in detail in the following.

Process 1

This process relates to one for preparing the compound (I) or its salt by reacting the compound (II) or its salt with the compound (III).

Suitable salts of the compounds(I) and (II) may include the same as those exemplified as pharmaceutically acceptable salts of the compound (I) hereinbefore.

The reaction may be preferably conducted in the presence of a base. Suitable base may be an inorganic base such as alkali or alkaline earth metal hydroxide (e.g. sodium hydroxide, potassium hydroxide, calcium hydroxide, etc.), alkali metal bicarbonate (e.g. sodium bicarbonate, potassium bicarbonate, etc.), alkali or alkaline earth metal carbonate (e.g. sodium carbonate, potassium carbonate, calcium carbonate, etc.), alkali metal phosphate (e.g. sodium dihydrogenphosphate, potassium dihydrogenphosphate, disodium hydrogenphosphate, dipotassium hydrogenphosphate, etc.) or an organic base such as alkali metal alkoxide (e.g. sodium methoxide, potassium ethoxide, etc.), amines (e.g. triethylamine, pyridine, lutidine, etc.).

The reaction is usually conducted in conventional manner. For example, the reaction is preferably conducted under cooling, at ambient temperature or under heating, and in conventional solvent which does not have an adverse influence on the reaction such as water, methanol, ethanol, propanol, N,N-dimethylformamide or an optional mixture thereof.

Process 2

This process relates to one for preparing the compound ($I^a$) or its salt by reacting the compound (IV) or its salt with the compound (V) or its salt.

Suitable salts of the compounds ($I^a$), (IV) and (V) may include the same as those exemplified as pharmaceutically acceptable salts of the compound (I).

This reaction may preferably be conducted in the presence of an acid or Lewis acid.

Suitable acids may include an organic acid (e.g. formic acid, acetic acid, propionic acid, etc.) and an inorganic acid (e.g. hydrochloric acid, hydrobromic acid, sulfuric acid, etc.) and suitable examples of Lewis acid are boron trihalide (e.g. boron trichloride, boron trifluoride, etc.), titanium tetrahalide (e.g. titanium tetrachloride, titanium tetrabromide, etc.), tin tetrahalide (e.g. tin tetrachloride, tin tetrabromide, etc.), aluminum halide (e.g. aluminum chloride, aluminum bromide, etc.), trihaloacetic acid (e.g. trichloroacetic acid, trifluoroacetic acid, etc.) or the like.

The reaction is usually conducted under cooling, at ambient temperature or under heating, and in conventional solvent which does not have an adverse influence on the reaction such as acetonitril, dioxane, benzene, hexane, chloroform, dichloromethane, tetrahydrofuran or the like.

Process 3

This process relates to one for preparing the compound ($I^b$) or its salt by reacting the compound (IV) or its salt with the compound (VI) or its salt.

Suitable salts of the compounds ($I^b$), (IV) and (VI) may include the same as those exemplified as pharmaceutically acceptable salts of the compound (I) hereinbefore.

This reaction is conducted in substantially the same manner as that of Process 2 and is to be referred thereto.

Process 4

This process relates to one for preparing the compound ($I^d$) or its salt by reacting the compound ($I^c$) or its salt with alkylating agents.

Suitable salts of the compounds (I$^c$) and (I$^d$) may include the same as those exemplified as pharmaceutically acceptable salts of the compound (I) hereinbefore.

Examples of alkylating agents include diazoalkanes (e.g., diazomethane, diazoethane, etc.), dialkyl sulphates (e.g., dimethyl sulphate, diethyl sulphate, dipropyl sulphate, etc.), alkyl halides (e.g., methyl iodide, ethyl iodide, propyl iodide, etc.) and the like.

The reaction is usually conducted in a conventional solvent which does not have an adverse influence on the reaction, for example, water, acetone, methanol, ethanol, benzene, toluene, dioxan, dichloromethane, N,N-dimethylformamide, dimethyl sulphoxide or the like, under cooling, at ambient temperature or under heating.

The reaction is preferably conducted in the presence of a base, examples of which include those given in the description of the Process 1.

Pharmaceutically acceptable salts of the compound (I) can be prepared by a conventional method, i.e., by treating the compound (I) with an acid. Preferred examples of said acid are the same as those exemplified in the explanation of pharmaceutically acceptable salts of the compound (I).

The starting compounds (III) and (IV) and their salts are novel and can be prepared, for example, according to Preparations as illustrated hereinafter or a similar manner thereto.

The object compound, dithioacetal compounds (I) and pharmaceutically acceptable salts thereof of this invention have 5-lipoxygenase-inhibiting activity (inhibiting activity of SRS-A synthesis), and are useful as an antiallergic agent oran antiinflammatory agent for human being and animals, and more particulary are useful for treatment of asthma, psoriasis, hepatitis, pancreatitis, arthritis, nephritis, inflammatory bowel disease, septic shock, arteriosclerosis, myocardial infarction, cerebral vasospasm or the like.

In order to illustrate the usefulness of the object compound (I), the pharmacological test data of the representative compounds of the object compound (I) are shown below.

Test: Inhibiting activity of SRS-A (Slow Reacting Substance of Anaphylaxis) synthesis in rat polymcrpholeukocyte (PMN) of using the calcium ionophore.

(1) Materials and Methods:

Preparation of PMN from rat

Male Spraque-Dawley rats weighing 250–300 g were anesthetized with ether and each was injected intraperitoneally with 20 ml of 0.1% glycogen (from Oyster). After 20 hours the rats were sacrificed and PMN were recovered in rinse of the peritoneal cavity with 10 ml Dulbeccos PBS (components in G/L: CaCl$_2$ 0.1, KH$_2$PO$_4$ 0.2, MgCl$_2$.6H$_2$O 0.1, NaCl 8.0, Na$_2$HPO$_4$.7-H$_2$O 2.16; pH 7.4). These rinses were filtered through nylon wool filter and centrifuged for 5 min at 1000 xg. The pellet was suspended in Dulbeccos PBS and centrifuged for 5 min at 1000 xg. The pellet was resuspended in Dulbeccos PBS and adjusted the cell concentration to 10$^7$ cells/ml with Dulbeccos PBS.

PMN stimulation

Samples were dissolved in ethanol and dispersed in Dulbeccos PBS to give a concentration of 10$^{-8}$ to 10$^{-3}$M. Antibiotic A23187; calcium ionophor (Dehring Diagnostics) (hereinafter referred to A23187) in DMSO (10 mM) was diluted with Dulbeccos PBS to give the concentration of 1 mM. Aliquots of the cell suspension (1×10$^7$ cells/ml, 0.98 ml) were equilibrated for 30 min at 37° C. Solution of sample(10 μl) was added and incubated for 15 min at 37° C. before the addition of 10 μl A23187 solution. Thus the final incubation volume of 1 ml contained approximately 1×10$^7$ cells, 10$^{-10}$ to 10$^{-5}$M samples and 10 μM A23187. Incubation with A23187 were continued for 15 min at 37° C. The reactions were terminated by setting the assay tubes in ice bath to chill as rapidly as possible to 4° C. The test tubes were centrifuged at 1500 xg for 5 min at 4° C. and decanted the supernatants into the tubes and kept cold prior to assaying.

Determination of immunoreactive LTC4 (i-LTC4)

The concentration of i-LTC4 in the cell-free supernatants from the incubations were determined by specific radioimmunoassay. The mean values of i-LTC4 (these incubations were carried out in duplicate) of each sample were calculated and the effect of samples on the synthesis of the leukotrienes was presented as a percentage of the value in the absence of samples.

(2) Results:

| Test Compound (Example No.) | IC$^{50}$ (M) |
| --- | --- |
| 1 | 3.0 × 10$^{-7}$ |
| 2 | 5.2 × 10$^{-7}$ |
| 3 | 3.9 × 10$^{-8}$ |
| 5 | 1.1 × 10$^{-7}$ |
| 6 | 1.3 × 10$^{-7}$ |
| 7 | 1.6 × 10$^{-7}$ |
| 8 | 3.3 × 10$^{-7}$ |
| 9 | 1.0 × 10$^{-7}$ |
| 10 | 1.1 × 10$^{-6}$ |
| 11 | 1.4 × 10$^{-6}$ |
| 16 | 1.1 × 10$^{-7}$ |
| 22 | 8.5 × 10$^{-7}$ |

Pharmaceutical compositions of this invention can be used in a conventional pharmaceutical forms such as powders, fine granules, granules, tablets, dragee, microcapsules, capsules, suppository, solution, suspension, emulsion, syrups and the like. If desired, diluents or disintegrators (e.g. sucrose, lactose, starch, crystalline cellulose, low-substituted hydroxypropyl cellulose, synthetic aluminum silicate, etc.), binding agents (e.g. cellulose, methylcellulose, hydroxypropylcellulose, hydroxypropylmethylcellulose, polypropylpyrrolidone, polyvinylpyrrolidone, gelatin, gum arabic, polyethyleneglycol, etc.), coloring agents, sweeting agents, lubricant (e.g. magnesium stearate, etc.) or the like, may be dispensed with said composition.

The dosage of said composition of this invention depends on the patient's age, body weight, condition, etc., and it is generally administered by the oral route at the daily dose level of 100 mg to 10 g as the object compound (I) or its pharmaceutically acceptable salt, preferably 1 g to 5 g on the same basis, at the interval of 1 to 3 times a day. Typical unit doses may be 50 mg, 100 mg, 200 mg, 500 mg, 1 g and the like, although these are only examples and not limitative, of course.

The following Preparations and Examples are given for the purpose of illustrating this invention.

Preparation 1

A mixture of 3-hydroxybenzaldehyde (6.71 g), 2-(chloromethyl)quinoline (8.88 g) and potassium carbonate (8.28 g) in N,N-dimethylformamide (25 ml) was stirred at 60° C. for 3 hours. The mixture was allowed to cool and concentrated in vacuo. The residue was treated with water. The separated oil was extracted with ethyl acetate. The organic layer was washed with brine, dried, and evaporated to give an oil, which was crystallized from n-hexane to yield 2-[[3-(formyl)-phenoxy]methyl]quinoline (12.5 g).

mp: 62°-63° C.

NMR (CDCl$_3$, δ): 5.45 (2H, s), 7.30 (1H, d, J=8 Hz), 7.45 (1H, t, J=8 Hz), 7.50 (1H, s), 7.52-7.62 (2H, m), 7.65 (1H, d, J=8 Hz), 7.76 (1H, t, J=8 Hz), 7.85 (1H, d, J=8 Hz), 8.10 (1H, d, J=8 Hz), 8.21 (1H, d, J=8 Hz), 10.00 (1H, s)

Following compounds were prepared according to a similar manner to that of Preparation 1.

Preparation 2

2-[[4-(Formyl)phenoxy]methyl]quinoline
mp: 88°-89° C.

NMR (CDCl$_3$, δ): 5.47 (2H, s), 7.12 (2H, d, J=8 Hz), 7.56 (1H, t, J=8 Hz), 7.64 (1H, d, J=8 Hz), 7.70-7.90 (4H, m), 8.10 (1H, d, J=8 Hz), 8.21 (1H, d, J=8 Hz), 9.88 (1H, s)

Preparation 3

2-[[2-(Formyl)phenoxy]methyl]quinoline
mp 100°-104° C.

NMR (CDCl$_3$, δ): 5.51 (2H, s), 7.00-7.20 (2H, m), 7.50-7.65 (2H, m), 7.71 (1H, d, J=8 Hz), 7.79 (1H, t, J=8 Hz), 7.88 (1H, d, J=8 Hz), 7.91 (1H, d, J=8 Hz), 8.11 (1H, d, J=8 Hz), 8.26 (1H, d, J=8 Hz), 10.70 (1H, s)

Preparation 4

3-[Bis(propylthio)methyl]-1-isopropoxybenzene (oil)

NMR (CDCl$_3$, δ): 0.95 (6H, t, J=7.4 Hz), 1.34 (6H, d, J=6.1 Hz), 1.43-1.67 (4H, m), 2.42-2.64 (4H, m), 4.50-4.62 (1H, m), 4.82 (1H, s), 6.78 (1H, dd, J=2.5, 7.8 Hz), 6.95-7.00 (2H, m), 7.21 (1H, t, J=7.8 Hz)

IR (Nujol): 1595, 1255, 985 cm$^{-1}$

Preparation 5

2-[[(5-Formyl-2-methoxy)phenoxy]methyl]quinoline
mp: 119°-120° C.

NMR (CDCl$_3$, δ): 4.00 (3H, s), 5.51 (2H, s), 7.04 (1H, d, J=8 Hz), 7.45-7.63 (3H, m), 7.69 (1H, d, J=8 Hz), 7.76 (1H, t, J=8 Hz), 7.83 (1H, d, J=8 Hz), 8.11 (1H, d, J=8 Hz), 8.20 (1H, d, J=8 Hz), 9.80 (1H, s)

IR (Nujol): 1665, 1595, 1580, 1505, 1435 cm$^{-1}$

EXAMPLE 1

A mixture of [3-bis(propylthio)methyl]phenol (900 mg), 2-(chloromethyl)benzothiazole (643 mg) and potassium carbonate (532 mg) in N,N-dimethylformamide (5 ml) was stirred at 60° C. for 3 hours. To the mixture was added water and the separated oil was extracted with ethyl acetate. The organic layer was washed with water, dried, and evaporated under reduced pressure to give an yellow oil, which was crystallized from n-hexane to yield 2-[[[3-bis(propylthio)methyl]phenoxy]methyl]benzothiazole (936 mg).

mp: 49°-51° C.

NMR (CDCl$_3$, δ): 0.93 (6H, t, J=7.4 Hz), 1.46-1.64 (4H, m), 2.39-2.61 (4H, m), 4.84 (1H, s), 5.50 (2H, s), 6.93-6.97 (1H, m), 7.08 (1H, d, J=7.7 Hz), 7.16-7.51 (4H, m), 7.90 (1H, dd, J=1.3 Hz and 7.4 Hz), 8.04 (1H, d, J=7.4 Hz)

EXAMPLE 2

2-[[[3-Bis(propylthio)methyl]phenoxy]methyl]pyridine hydrochloride was prepared according to a similar manner to that of Example 1 and by treating the object compound, 2-[[[3-bis(propylthio)methyl]phenoxy]methyl]pyridine with dry hydrogen chloride in ethyl ether.

mp: 74°-76° C.

NMR (CD$_3$OD, δ): 0.94 (6H, t, J=7.3 Hz), 1.51-1.62 (4H, m), 2.45-2.61 (4H, m), 4.97 (1H, s), 5.56 (2H, s), 7.07 (1H, dd, J=2.4 Hz and 7.8 Hz), 7.72 (1H, d, J=7.7 Hz), 7.26-7.37 (2H, m), 8.09 (1H, t, J=8.4 Hz and 5.8 Hz), 8.2 (1H, d, J=8.0 Hz), 8.68 (1H, t, J=8.0 Hz and 8.4 Hz), 8.88 (1H, d, J=5.8 Hz)

EXAMPLE 3

To a cooled mixture of 2-[[3-(formyl)phenoxy]methyl]quinoline (5.26 g) and 1-propanthiol (4 ml) in dry acetonitrile (30 ml) in an ice bath was added dropwise boron trifluoride etherate (3.7 ml) in a few minutes. The mixture was stirred at 0° C. for one hour and then dry ethyl ether (150 ml) was added thereto. The separated solid was collected by filtration, washed with ethyl ether, and dissolved in a mixture of ethyl ether and aqueous 1N-sodium hydroxide solution. The organic layer was washed with brine, dried, and evaporated under reduced pressure. The residue was dissolved in dry ethyl ether (50 ml) and treated with dry hydrogen chloride to yield 2-[[[3-bis(propylthio)-methyl]phenoxy]methyl]quinoline hydrochloride (5.69 mg)

mp: 71°-72° C.

NMR (DMSO-d$_6$, δ): 0.86 (6H, t, J=6 Hz), 1.45 (4H, m), 2.43 (4H, m), 5.07 (1H, s), 5.58 (2H, s), 7.02 (1H, d, J=8 Hz), 7.07 (1H, d, J=8 Hz), 7.18 (1H, s), 7.30 (1H, t, J=8 Hz), 7.78 (1H, t, J=8 Hz), 7.92 (1H, d, J=8 Hz), 7.99 (1H, t, J=8 Hz), 8.19 (1H, d, J=8 Hz), 8.28 (1H, d, J=8 Hz), 8.80 (1H, d, J=8 Hz)

Following compounds were prepared according to a similar manner to that of Example 3.

EXAMPLE 4

2-[[[2-Bis(propylthio)methyl]phenoxy]methyl]quinoline hydrochloride
mp: 127°-129° C.

NMR (DMSO-d$_6$, δ): 0.83 (6H, t, J=6 Hz), 1.50 (4H, m), 2.51 (4H, m), 5.52 (1H, s), 5.58 (2H, s), 7.02 (1H, t, J=8 Hz), 7.14 (1H, d, J=8 Hz), 7.37 (1H, t, J=8 Hz), 7.55 (1H, d, J=8 Hz), 7.75 (1H, t, J=8 Hz), 7.89 (1H, d, J=8 Hz), 7.94 (1H, t, J=8 Hz), 8.15 (1H, d, J=8 Hz), 8.21 (1H, d, J=8 Hz), 8.74 (1H, d, J=8 Hz)

EXAMPLE 5

2-[[[4-Bis(propylthio)methyl]phenoxy]methyl]quinoline hydrochloride
mp: 120°-121° C.

NMR (DMSO-d$_6$, δ): 0.88 (6H, t, J=6 Hz), 1.50 (4H, m), 2.48 (4H, m), 5.05 (1H, s), 5.51 (2H, s), 7.06 (2H, d, J=8 Hz), 7.39 (2H, d, J=8 Hz), 7.75 (1H, t, J=8 Hz), 7.87 (1H, d, J=8 Hz), 7.94 (1H, t, J=8 Hz), 8.15 (1H, d, J=8 Hz), 8.22 (1H, d, J=8 Hz), 8.13 (1H, d, J=8 Hz)

EXAMPLE 6

2-[[[3-Bis(ethylthio)methyl]phenoxy]methyl]quinoline hydrochloride
mp: 114°-115° C.

NMR (CD$_3$OD, δ): 1.48 (6H, t, J=7 Hz), 2.43-2.60 (4H, m), 5.00 (1H, s), 5.65 (2H, s), 7.02 (1H, d, J=8 Hz), 7.11 (1H, d, J=8 Hz), 7.27 (1H, s), 7.31 (1H, t, J=8 Hz), 7.90 (1H, t, J=8 Hz), 8.08 (1H, d, J=8 Hz), 8.10 (1H, t, J=8 Hz), 8.27 (1H, d, J=8 Hz), 8.31 (1H, d, J=8 Hz), 9.01 (1H, d, J=8 Hz)

EXAMPLE 7

2-[[[3-Bis(butylthio)methyl]phenoxy]methyl]quinoline hydrochloride mp: 79°-80° C.

NMR (CD$_3$OD, δ): 0.86 (6H, t, J=7 Hz), 1.24–1.57 (8H, m), 2.45–2.60 (4H, m), 4.96 (1H, s), 5.74 (2H, s), 7.09 (1H, d, J=8 Hz), 7.13 (1H, d, J=8 Hz), 7.29 (1H, s), 7.33 (1H, t, J=8 Hz), 7.98 (1H, t, J=8 Hz), 8.18 (1H, d, J=8 Hz), 8.20 (1H, t, J=8 Hz), 8.35 (1H, d, J=8 Hz), 8.39 (1H, d, J=8 Hz), 9.17 (1H, d, J=8 Hz)

EXAMPLE 8

2-[[[3-Bis(pentylthio)methyl]phenoxy]methyl]quinoline hydrochloride mp: 89°-90° C.

NMR (DMSO-d$_6$, δ): 0.82 (6H, t, J=6 Hz), 1.10–1.35 (8H, m), 1.53 (4H, m), 2.43 (4H, m), 5.07 (1H, s), 5.53 (2H, s), 7.00 (1H, d, J=8 Hz), 7.05 (1H, d, J=8 Hz), 7.16 (1H, s), 7.30 (1H, t, J=8 Hz), 7.75 (1H, t, J=8 Hz), 7.87 (1H, d, J=8 Hz), 7.94 (1H, t, J=8 Hz), 8.15 (1H, d, J=8 Hz), 8.24 (1H, d, J=8 Hz), 8.73 (1H, d, J=8 Hz)

EXAMPLE 9

2-[[[3-Bis(isopropylthio)methyl]phenoxy]methyl]quinoline hydrochloride mp: 152°-154° C.

NMR (CD$_3$OD, δ): 1.16 (6H, d, J=7 Hz), 1.21 (6H, d, J=7 Hz), 2.82–2.96 (2H, m), 5.03 (1H, s), 5.72 (2H, s), 7.10 (1H, d, J=8 Hz), 7.15 (1H, d, J=8 Hz), 7.31 (1H, s), 7.33 (1H, t, J=8 Hz), 7.98 (1H, t, J=8 Hz), 8.17 (1H, d, J=8 Hz), 8.19 (1H, t, J=8 Hz), 8.34 (1H, d, J=8 Hz), 8.37 (1H, d, J=8 Hz), 9.16 (1H, d, J=8 Hz)

EXAMPLE 10

2-[[[3-Bis(phenylthio)methyl]phenoxy]methyl]quinoline hydrochloride mp: 143°-145° C.

NMR (DMSO-d$_6$, δ): 5.51 (2H, s), 6.11 (1H, s), 6.99 (1H, d, J=8 Hz), 7.13 (1H, d J=8 Hz), 7.15–7.40 (12H, m), 7.77 (1H, t, J=8 Hz), 7.83 (1H, d, J=8 Hz), 7.96 (1H, t, J=8 Hz), 8.17 (1H, d, J=8 Hz), 8.25 (1H, d, J=8 Hz), 8.75 (1H, d, J=8 Hz)

EXAMPLE 11

2-[[[3-Bis(benzylthio)methyl]phenoxy]methyl]quinoline mp: 90°-91° C.

NMR (CDCl$_3$, δ): 3.56 (2H, d, J=14 Hz), 3.78 (2H, d, J=14 Hz), 4.47 (1H, s), 5.40 (2H, s), 6.90–7.00 (2H, m), 7.05–7.35 (12H, m), 7.57 (1H, t, J=8 Hz), 7.41 (1H, d, J=8 Hz), 7.77 (1H, t, J=8 Hz), 7.86 (1H, d, J=8 Hz), 8.12 (1H, d, J=8 Hz), 8.23 (1H, d, J=8 Hz)

Following compounds were prepared according to a similar manner to that of Example 1.

EXAMPLE 12

2-[[[3-Bis(propylthio)methyl]phenoxy]methyl]-5-methoxybenzothiazole (oil)

NMR (CDCl$_3$, δ): 0.94 (6H, t, J=7 Hz), 1.56 (4H, m), 2.51 (4H, m), 3.91 (3H, s), 4.83 (1H, s), 5.48 (2H, s), 6.95 (1H, d, J=8 Hz), 7.06 (1H, d, J=8 Hz), 7.08 (1H, d, J=8 Hz), 7.17 (1H, s), 7.27 (1H t, J=8 Hz), 7.52 (1H, s), 7.73 (1H, d, J=8 Hz)

IR (Nujol): 1595, 1575, 1480, 1320, 1255, 1150 cm$^{-1}$

EXAMPLE 13

2-[[[3-Bis(propylthio)methyl]phenoxy]methyl]-5-chlorobenzothiazole mp: 86°-88° C.

NMR (CDCl$_3$, δ): 0.96 (6H, t, J=7.4 Hz), 1.49–1.67 (4H, m), 2.45–2.61 (4H, m), 4.86 (1H, s), 5.50 (2H, s), 6.92–8.04 (7H, m)

EXAMPLE 14

2-[[[3-Bis(propylthio)methyl]phenoxy]methyl]benzoxazole (oil)

NMR (CDCl$_3$, δ): 0.96 (6H, t, J=7.3 Hz), 1.49–1.67 (4H, m), 2.41–2.60 (4H, m), 4.86 (1H, s), 5.36 (2H, s), 6.99 (1H, dd, J=2.5, 7.8 Hz), 7.11 (1H, d, J=7.8 Hz), 7.21 (1H, d, J=2.5 Hz), 7.29 (1H, t, J=7.8 Hz), 7.37–744 (2H, m), 7.57–7.61 (1H, m), 7.77–7.81 (1H, m)

IR (Nujol): 1595, 1580, 1260, 1145 cm$^{-1}$

EXAMPLE 15

2-[[[3-Bis(propylthio)methyl]phenoxy]methyl]quinazoline (oil)

NMR (CDCl$_3$, δ): 0.93 (6H, t, J=7.1 Hz), 1.53 (4H, m), 2.47 (4H, m), 4.82 (1H, s), 5.51 (2H, s), 6.95–7.08 (2H, m), 7.21 (1H, s), 7.27 (1H, d, J=6.5 Hz), 7.68 (1H, m), 8.00–8.10 (2H, m), 8.09 (1H, m) 9.43 (1H, s)

IR (CHCl$_3$): 2975, 2860, 1620, 1580, 1490, 1385, 1260, 1150 cm$^{-1}$

EXAMPLE 16

2-[[[3-Bis(isopropylthio)methyl]phenoxy]methyl]benzothiazole mp: 109°110° C.

NMR (CDCl$_3$, δ): 1.19 (6H, d, J=6.0 Hz), 1.23 (6H, d, J=6.0 Hz), 2.92 (2H, m), 4.91 (1H, s), 5.50 (2H, s), 6.94 (1H, d, J=7.7 Hz), 7.12 (1H, d, J=7.7 Hz), 7.21–7.31 (2H, m), 7.37 –7.54 (2H, m), 7.91 (1H, d, J=6.7 Hz), 8.04 (1H, d, J=6.7 Hz)

IR Nujol): 2925, 2850, 1605, 1475, 1465, 1270, 760 cm$^{-1}$

EXAMPLE 17

2-[[[3-Bis(propylthio)methyl]phenoxy]methyl]naphthalene (oil)

NMR (CDCl$_3$, δ): 0.99 (6H, t, J=7.3 Hz), 1.53–171 (4H, m), 2.46–2.68 (4H, m), 4.88 (1H, s), 5.53 (2H, s), 6.99 (1H, d, J=8.2 Hz), 7.09 (1H, d, J=7.6 Hz), 7.22–7.67 (6H, m), 7.88–7.96 (2H, m), 8.10 (1H, d, J=9.4 Hz)

IR (Nujol): 1595, 1585, 1240, 1045 cm$^{-1}$

EXAMPLE 18

2-[[[3-Bis(propylthio)methyl]phenoxy]methyl]-5-bromo-4-phenylthiazole mp: 41°-42° C.

NMR (CDCl$_3$, δ): 0.99 (6H, t, J=7 Hz), 1.47–170 (4H, m), 2.40–267 (4H, m), 4.85 (1H, s), 5.36 (2H, s), 6.91 (1H, dd, J=2, 8 Hz), 7.07–7.55 (7H, m), 7.94 (1H, d, J=8 Hz)

EXAMPLE 19

A mixture of [3-bis(propylthio)methyl]phenol (180 mg), 2-chloromethylimidazo[1,2-a]pyridine (117 mg) and potassium carbonate (107 mg) in N,N-dimethylformamide (1 ml) was stirred at 80° C. for 40 minutes. The reaction mixture was allowed to cool to ambient temperature, followed by addition of water. The separated oil was extracted with ethyl acetate. The organic layer was dried and concentrated in vacuo to give a brown oil (230 mg) which was purified by columnchromatography on silica gel, eluting with 1% methanol in methylene chloride. The resulting colorless oil dissolved in a little amount of ethyl ether was treated with hydrogen chloride in ethyl acetate to give 2-[[[3-bis(propylthio)methyl]phenoxy]methyl]imidazo[1,2-a]pyridine hydrochloride (130 mg).

mp: 75°–80° C.

NMR (CD$_3$OD, δ): 0.92 (6H, t, J=7 Hz), 1.54 (4H, m), 2.51 (4H, m), 4.95 (1H, s), 5.41 (2H, s), 7.01 (1H, d, J=8 Hz), 7.09 (1H, d, J=8 Hz), 7.20 (1H, d, J=8 Hz), 7.29 (1H, t, J=8 Hz), 7.49 (1H, t, J=7 Hz), 7.85–8.05 (2H, m), 8.31 (1H, s), 8.80 (1H, d, j=7 Hz)

IR (Nujol): 3470, 3400, 3100, 1655, 1600, 1580, 1525, 1480, 1255 cm$^{-1}$

Following compounds were prepared according to a similar manner to that of Example 19.

EXAMPLE 20

2-[[3-Bis(propylthio)methyl]phenoxy]quinoline hydrochloride mp: 108°14 110° C.

NMR (DMSO-d$_6$, δ): 0.89 (6H, t, J=6 Hz), 1.52 (4H, m), 2.53 (4H, m), 5.18 (1H, s), 7.17 (1H, d, J=8 Hz), 7.25–7.75 (7H, m), 7.96 (1H, d, J=8 Hz), 8.43 (1H, d, J=8 Hz)

IR (Nujol): 1640, 1595, 1390, 1305, 1280, 1250, 1245, 755 cm$^{-1}$

EXAMPLE 21

3-[Bis(propylthio)methyl]-1-(2-N,N-dimethylaminoethoxy)benzene hydrochloride mp: 94°–96° C.

NMR (CDCl$_3$, δ): 0.93 (6H, t, J=7.3 Hz), 1.47–1.65 (4H, m), 2.40–2.63 (4H, m), 2.97 (6H, s), 3.59 2H, t, J=4.8 Hz), 4.35 (2H, t, J=4.8 Hz), 4.94 (1H, s)), 6.93 (1H, dd, J=2.5, 7.8 Hz), 7.08 (1H, t, J=7.8 Hz), 7.15 (1H, d, J=2.5 Hz), 7.27 (1H, t, J=7.8 Hz)

IR (Nujol): 2590, 1260, 1150, 1025 cm$^{-1}$

EXAMPLE 22

2-[[[3-Bis(propylthio)methyl]phenoxy]methyl]quinazoline hydrochloride was prepared by treating 2-[[[3-bis(propylthio)methyl]phenoxy]methyl]quinazoline with hydrogen chloride in ethyl ether.

mp: 104°–105° C. (decomp.)

NMR (CD$_3$OD, δ): 0.92 (3H, t, J=6.2 Hz), 0.94 (3H, t, J=6.2 Hz), 1.41–1.65 (4H, m), 2.73–2.63 (4H, m), 4.98 (1H, s), 5.31 (2H, s), 6.21 (1H, s), 7.06 (1H, dd, J=2.0, 8.7 Hz), 7.16 (1H, d, J=8.7 Hz), 7.28–7.65 (6H, m)

IR (Nujol): 2925, 2850, 1650, 1585, 1465, 1320, 1285, 750 cm$^{-1}$

Following compounds were prepared according to a similar manner to that of Example 3.

EXAMPLE 23

2-[[[5-Bis(propylthio)methyl]-2-methoxyphenoxy]methyl]quinoline hudrochloride mp: 119°–120° C.

NMR (DMSO-d$_6$, δ): 0.79 (6H, t, J=7 Hz), 1.39 (4H, m), 2.35 (4H, m), 3.82 (3H, s), 5.00 (1H, s), 5.55 (2H, s), 7.01 (2H, s), 7.19 (1H, s), 7.80 (1H, t, J=8 Hz), 7.90 (1H, d, J=8 Hz), 7.99 (1H, t, J=8 Hz), 8.19 (1H, d, J=8 Hz), 8.28 (1H, d, J=8 Hz), 8.80 (1H, d, J=8 Hz)

IR (Nujol): 2250, 1975, 1595, 1505, 1410 cm$^{-1}$

EXAMPLE 24

2-[[[3-Bis(propylthio)methyl]phenoxy]methyl]benzimidazole hydrochloride mp: 130°–133° C.

NMR (DMSO-d$_6$, δ): 0.85 (6H, t, J=7 Hz), 1.48 (4H, m) 2.46 (4H, m), 5.12 (1H, s), 5.67 (2H, s), 7.06–7.85 (8H, m)

IR (Nujol): 2750–2300, 1605, 1265, 900 cm$^{-1}$

EXAMPLE 25

To a cooled mixture of 2-[[3-(formyl)phenoxy]methyl]quinoline (1.05 g) and 1,3-propanedithiol (0.98 ml) in dry acetonitrile (10 ml) in an ice bath was added dropwise 2N-hydrogen chloride in ethyl acetate and then dry ethyl ether (100 ml) was added thereto. The supernatant was discarded and the syrupy residue was washed with dry ethyl ether twice. The residue was dissolved in methanol (30 ml) and then aqueous 1N-sodium hydroxide solution (10 ml) was added dropwise thereto at 0° C. To the mixture were added methylene chloride (100 ml) and water (80 ml) and then the separated organic layer was dried and evaporated in vacuo to give a syrup (1.60 g), which was purified by column chromatography on silica gel (elution by methylene chloride) to give the objective product (1.04 g) as a colorless syrup. The syrup (910 mg) was crystallized from ethyl ether to yield 2-[[3-(1,3-dithian-2-yl)phenoxy]methyl]quinoline (740 mg) as white powders.

mp: 92°–93° C.

NMR (CDCl$_3$, δ): 1,95 (1H, m) 2.17 (1H, m), 2.88–2.93 (2H, m), 3.01–3.09 (2H, m), 5.13 (1H, s), 5.38 (2H, s), 6.95 (1H, s), 7.25 (1H, t, J=8 Hz), 7.55 (1H, t, J=8 Hz), 7.68 (1H, d, J=8 Hz), 7.74 (1H, t, J=8 Hz), 7.83 (1H, d, J=8 Hz), 8.08 (1H, d, J=8 Hz), 8.20 (1H, d, J=8 Hz)

IR (Nujol): 1596, 1273, 1156 cm$^{-1}$

EXAMPLE 26

A mixture of 2-[[[3-bis(propylthio)methyl]phenoxy]methyl]benzimidazole hydrochloride (480 mg), methyl iodide (356 mg) and potassium carbonate (169 mg) in N,N-dimethylformamide (6 ml) was stirred for 3 hours at ambient temperature and then for 1.5 hours at 40° C. The mixture was cooled to ambient temperature and poured into a mixture of ice-water and ethyl ether. The organic layer was separated and extracted with 1N hydrochloric acid. After adjustment to pH 8 with sodium bicarbonate, the aqueous layer was extracted with methylene chloride. The organic layer was dried and evaporated in vacuo to give an oily residue (190 mg), with a mixture of benzene and acetone (8.5:1.5 (V/V)), to yield an oily product (100 mg). To a solution of the product in ethyl acetate (2 ml) was added 2N-hydrogen chloride in ethyl acetate (0.5 ml) to give white precipitates, which were collected by filtration and washed with ethyl acetate to yield 2-[[[3-bis-(propylthio)methyl]phenoxy]methyl]-1-methylbenzimidazole hydrochloride (85 mg) as white crystals.

mp: 148°–149° C.

NMR (DMSO-d$_6$, δ): 0.87 (6H, t, J=6 Hz), 1.50 (4H, m), 2.47 (4H, m), 4.05 (3H, s), 5.12 (1H, s), 5.74 (2H, s), 7.11–8.00 (8H, m)

EXAMPLE 27

3-[Bis(propylthio)methyl]-1-isopropoxybenzene (oil) was prepared according to a similar manner that of Example 1.

NMR (CDCl₃, δ): 0.95 (6H, t, J=7.4 Hz), 1.34 (6H, d, J=6.1 Hz), 1.43–1.67 (4H, m), 2.42–2.64 (4H, m), 4.50–4.62 (1H, m), 4.82 (1H, s), 6.78 (1H, dd, J=2.5, 7.8 Hz), 6.95–7.00 (2H, m), 7.21 (1H, t, J=7.8 Hz),

IR (Nujol): 1595, 1255, 985 cm⁻¹

We claim:

1. A dithioacetal compound of the formula:

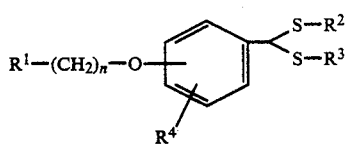

wherein R¹ is a heterocyclic group of the formula

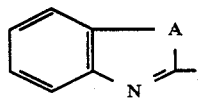

wherein A is

—O— or —S—, which may have one or more substituents selected from halogen, lower alkyl, lower alkoxy and phenyl, R² and R³ are each lower alkyl, aryl or ar-(lower)alkyl, or R² and R³ are together to form 1,3-dithian ring, R⁴ is hydrogen or lower alkoxy, and n is 0 or an integer 1 to 4 and pharmaceutically aceeptable salts thereof.

2. A compound according to claim 1, wherein R¹ is

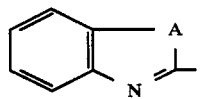

wherein A is

n is ,

R² and R³ are each lower alkyl, and R⁴ is hydrogen.

3. A compound according to claim 1, wherein the compound is represented by the following formula:

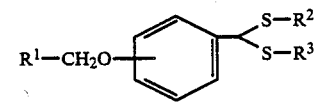

wherein R¹ is as defined in claim 1, wherein A in R¹ is —O—, and R² and R³ are each lower alkyl.

4. A compound according to claim 1, wherein the compound is represented by the following formula:

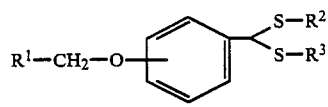

wherein R¹ is a heterocyclic group of the formula:

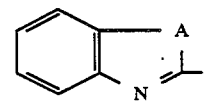

which may have one or more substituents selected from halogen, lower-alkyl, lower alkoxy and phenyl, wherein A is

—O— or —S—, and R² and R³ are each lower alkyl.

5. A compound according to claim 4, wherein R¹ is a heterocyclic group of the formula:

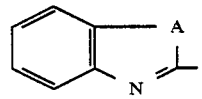

wherein A is

—O— or —S—, and R² and R³ are each lower alkyl.

6. A compound according to claim 5, wherein R¹ is benzothiazolyl, and R² and R³ are each propyl.

7. A compound according to claim 5 wherein A is —O— or —S—.

8. A compound according to claim 4 wherein A is —S—.

9. A compound according to claim 5 wherein A is —S—.

10. A pharmaceutical composition comprising as an active ingredient a compound as defined in claim 1 or its pharmaceutically acceptable salt.

11. An antiinflammatory agent or antiallergic agent comprising as an active ingredient a compound as defined in claim 1 or its pharmaceutically acceptable salt.

* * * * *